United States Patent [19]

Halvorsen, Jr. et al.

[11] Patent Number: 5,337,596

[45] Date of Patent: Aug. 16, 1994

[54] APPARATUS FOR MEASURING PERMEABILITY OF A ROCK SAMPLE

[75] Inventors: Christian Halvorsen, Jr., Forus, Norway; Andrew R. Hurst, Virginia Beach, England

[73] Assignee: Den Norske Stats Oljeselskap A.S, Stavanger, Norway

[21] Appl. No.: 941,438

[22] PCT Filed: Mar. 26, 1991

[86] PCT No.: PCT/NO91/00049
§ 371 Date: Oct. 30, 1992
§ 102(e) Date: Oct. 30, 1992

[87] PCT Pub. No.: WO91/15749
PCT Pub. Date: Oct. 17, 1991

[30] Foreign Application Priority Data

Apr. 3, 1990 [NO] Norway ................................. 901499

[51] Int. Cl.[5] ............................................. G01N 15/08
[52] U.S. Cl. ............................................................ 73/38
[58] Field of Search ............................................... 73/38

[56] References Cited

U.S. PATENT DOCUMENTS

| | | | |
|---|---|---|---|
| 4,573,342 | 3/1986 | Jones | 73/38 |
| 4,864,845 | 9/1989 | Chandler et al. | 73/38 |
| 5,237,854 | 8/1993 | Jones | 73/38 |

*Primary Examiner*—Hezron E. Williams
*Assistant Examiner*—Joseph W. Roskos
*Attorney, Agent, or Firm*—Foley & Lardner

[57] ABSTRACT

Apparatus for measuring permeability in rock samples comprising a measuring table (1, 41) for strapping down a rock sample (2), a nozzle (18) that can be pressed against the rock sample (2) at a set force, a gas source (23) connected to the nozzle (18), devices (24) for measuring mass flow through the nozzle and pressure in the nozzle. The apparatus comprises a rack (10, 48) equipped with a pneumatic cylinder to which the nozzle is attached and where the rack and measuring table are movable in relation to each other in an X and Y direction via motors. A computer (21) that controls: (a) the motors, and thereby the movements of the nozzle and the measuring table relatively to each other so that the sample is covered by a predetermined measuring point pattern, (b) a mass flow meter (24) that controls and measures the gas flow to the nozzles, (c) a selector valve for compressed air that controls the pneumatic cylinder, and thereby the vertical movement of the nozzle.

7 Claims, 3 Drawing Sheets

APPARATUS FOR MEASURING PERMEABILITY OF A ROCK SAMPLE

TECHNICAL FIELD

The invention relates to an apparatus for measuring permeability in rock samples comprising a measuring table for strapping down a rock sample, a nozzle that can be pressed against the rock sample at a set force, a gas source connected to the nozzle, devices for measuring mass flow through the nozzle and pressure in the nozzle.

BACKGROUND ART

It is a well-known fact that measuring the conductivity and porosity of a formation is important when determining whether the formation contains hydrocarbons, as hydrocarbons are found as non-conductive fluids in porous rock formations. It is also a well-known fact that hydrocarbons usually cannot be recovered from porous rock formations unless the formations also are permeable. It is therefore important to have reliable measurements of the formations permeability. These measurements are best taken in an apparatus in a laboratory.

Known apparatuses of the type mentioned above are operated manually. This makes the measuring cumbersome and expensive.

DISCLOSURE OF INVENTION

It is an object of the invention to provide an apparatus that can make these measurements automatically.

This has been achieved according to the invention with an apparatus that is characterised by a rack equipped with a pneumatic cylinder to which the nozzle is attached and where the rack and measuring table are movable in relation to each other along the X and Y axes via motors and a computer that controls:

a) the motors, and thereby the movements of the nozzle and the measuring table relatively to each other that the sample is covered by a predetermined measuring point pattern.

b) a mass flow meter that controls and measures the gas flow to the nozzles c) a selector valve for compressed air that controls the pneumatic cylinder, and thereby the vertical movement of the nozzle

BRIEF DESCRIPTION OF DRAWINGS

The invention will be described in further detail below with reference to the enclosed figures where.

MODES FOR CARRYING OUT THE INVENTION

Figure 1:
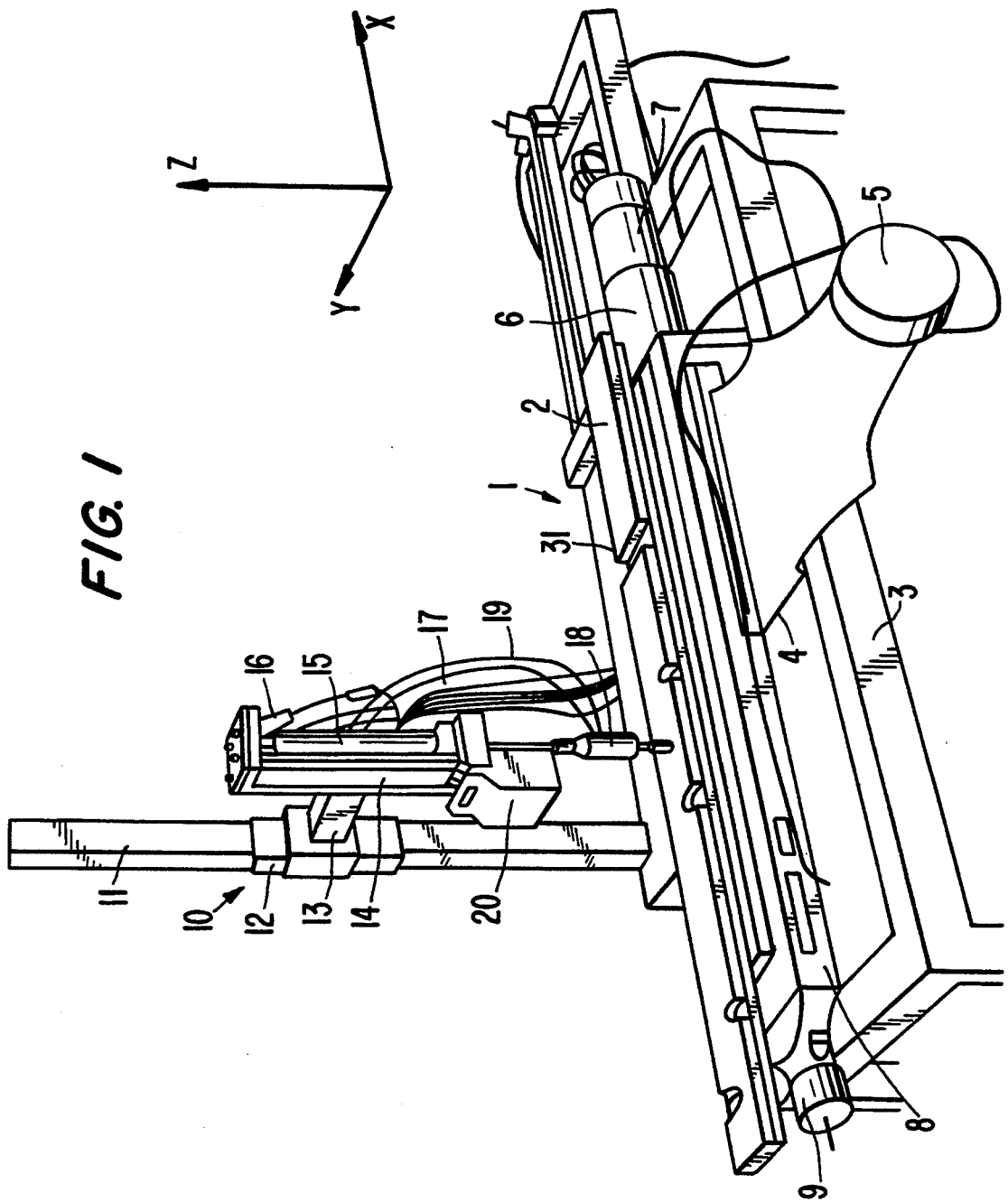
FIG. 1 shows a drawing of the apparatus according to the invention.

FIG. 1 shows a measuring table 1 which is provided for clamping one or several rock samples 2 where permeability is to be measured. The shown measuring table 1 is placed on a support structure 3 and comprises a bottom frame 4 which is rigidly connected to the support structure and comprises a first driving motor 5, an intermediate frame 6 which comprises a second driving motor 7 and is mounted so it can be moved along a Y axis in relation to the bottom frame, and an upper frame 8 which is movable along an X axis in relation to the intermediate frame 6.

The driving motor 5 of the bottom frame 4 works a positioning screw (not shown) oriented in the Y direction which runs through at least one threaded bushing on the intermediate frame 6. The intermediate frame 6 is mounted in a sliding position in relation to the bottom frame via grooves or guide bars that slide the intermediate frame in the Y direction upon rotation of the positioning screw.

The driving motor 7 of the intermediate frame 6 comprises a positioning screw (not shown) oriented along the X axis and which on its other side is pivotally mounted in a revolving position in a bushing 9. The positioning screw runs through at least one threaded bushing which is connected to the upper frame 8. The upper frame 8 is mounted in a sliding position in relation to the intermediate frame via grooves or guide bars that slide the upper frame in the X direction upon rotation of the positioning screw.

The top of the upper frame 8 is designed approximately level and arranged to receive the above-mentioned rock samples. In the trade it is usual for the rock samples 2 to be glued to wooden boards of standard size. The wooden boards can be secured to the upper frame, basically using known mechanical fastening devices.

For our purpose electrical driving motors that are commercially available are preferred. They should enable movement of the frames with a high degree of positioning accuracy. The motors can be controlled on the basis of logical signals which, according to this invention, come from a computer. In the same manner the rotation of the motors and thereby the movement of the rock samples can be measured accurately, and these data can be stored in the computer.

A rack 10 is also secured to the support structure 3 and it consists of a vertical post 11 and a sliding sleeve 12 which can be moved along the vertical post 11. A horizontal arm 13 is secured to the sliding sleeve 12. Via a mounting bracket 14 the horizontal arm 13 carries a pneumatically driven cylinder 15. The mounting bracket 14 is positioned so that it protrudes over the area where the rock sample is placed. The cylinder 15 is connected to a compressed air source via two compressed air lines 16, 17, which are connected to the bottom and top part respectively of a piston in the cylinder 15. A nozzle 18 is connected to the cylinder's movable piston and can via the pneumatic cylinder 15 be pressed against the rock sample 2 at the desired and preferably constant force.

In order to measure samples that are longer than the movable area for the upper frame, in one operation, the rack 10 is mounted in a sliding position on a horizontal beam 31. The rack can, in a preferred design, be moved between two positions using a not shown pneumatically driven piston-cylinder arrangement.

The nozzle 18 is connected to a gas source via a line 19, and the gas used is in preferably nitrogen gas. The flow rate of the gas that is flooded into the sample is measured by a commercially available mass flow meter. The flow rate is controlled by one or more mass flow controllers, which may consist of separate control valves or control valves that comprise an integrated part of the mass flow meter. Both parts are available on the market. In practice the gas flow will be controlled so that either constant pressure or constant flow rate is maintained in the line 19.

If constant pressure is chosen, line 19 is also equipped with one or more pressure gauges.

By controlling the mass flow controllers with the aid of the computer, and using pressure and mass flow measurements as control parameters, there is the possibility of implementing series of permeability measurements either under constant pressure or at a constant flow rate.

In order to obtain reliable permeability measurements one must avoid taking measurements near the edge of the sample, while at the same time avoiding taking measurements in places where there are holes in the rock sample. To solve this problem the preferred design of the invention has a measuring device 20 that is secured to the above-mentioned rack, and which can record variation in vertical distance to an underlying surface. When the thickness and maximum surface roughness have been defined, a connected computer can calculate the positions of the sample's circumference and holes in the rock samples, and said measuring positions can be stored in the computer's memory. A preferred, commercially available device for conducting these measurements uses a high-frequency beam of light that is transmitted from a light source and where the reflecting light is received via an optical detector and a linear photodetector. On the basis of the transmitted and received signals the distance to the measured surface can be calculated and stored in the computer's memory. A device that is able to perform this task is marketed by LIMAB and is called "Precimeter".

Figure 2:
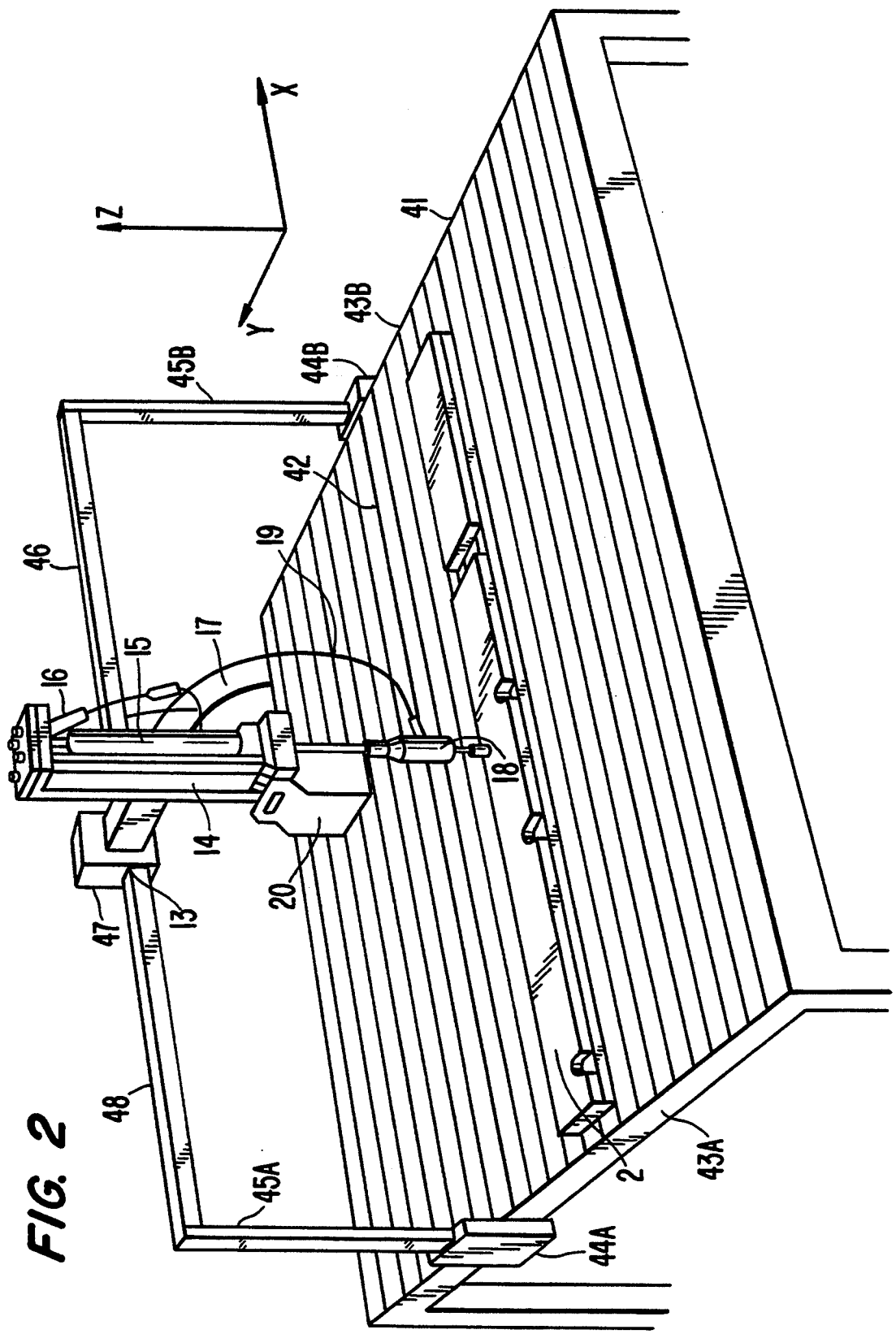
FIG. 2 shows a drawing of an alternative construction of the apparatus according to the invention.

FIG. 2 shows an alternative design of the apparatus. The horizontal arm 13, the mounting bracket 14, the cylinder 15, the compressed air lines 16, 17, the nozzle 18, the line 19 and the measuring device 20 are identical to the components shown in FIG. 1, and have been given the same reference numbers. The mode of operation is also identical and will not be further described here.

In the design shown in FIG. 2 the apparatus comprises a measuring table 41 with an approximately level table surface 42. The table surface is preferably arranged so that one or several rock samples 2 can be secured when measuring permeability.

Along the side edges 43A, 43B of the table 41 there are mountings for two carriages 44A, 44B, where at least one of the carriages comprises a motor for movement along the table in the directions of the Y axis. Vertical posts 45A, 45B protrude from each of the carriages 44A, 44B. The upper ends of the posts are connected to a horizontal beam 46. The posts 45A, 45B and the horizontal beam 46 will in the following be called rack 48. A movable carriage 47 is mounted on the horizontal beam 46. A built-in motor (not shown) in the carriage 47 makes it possible to drive the carriage 47 in the directions of the X axis along the beam 46. The horizontal arm 14 is rigidly connected to the carriage 47.

Two electric driving motors are preferred for movement of the rack. These are commercially available and are of a type that enable movement of the frames with a high degree of positioning accuracy. The motors can be controlled on the basis of logical signals which, in this invention, come from a computer. In the same manner the rotation of the motors and thereby the movement of the rock sample can be measured accurately, and these data can be stored in the computer.

Figure 3:
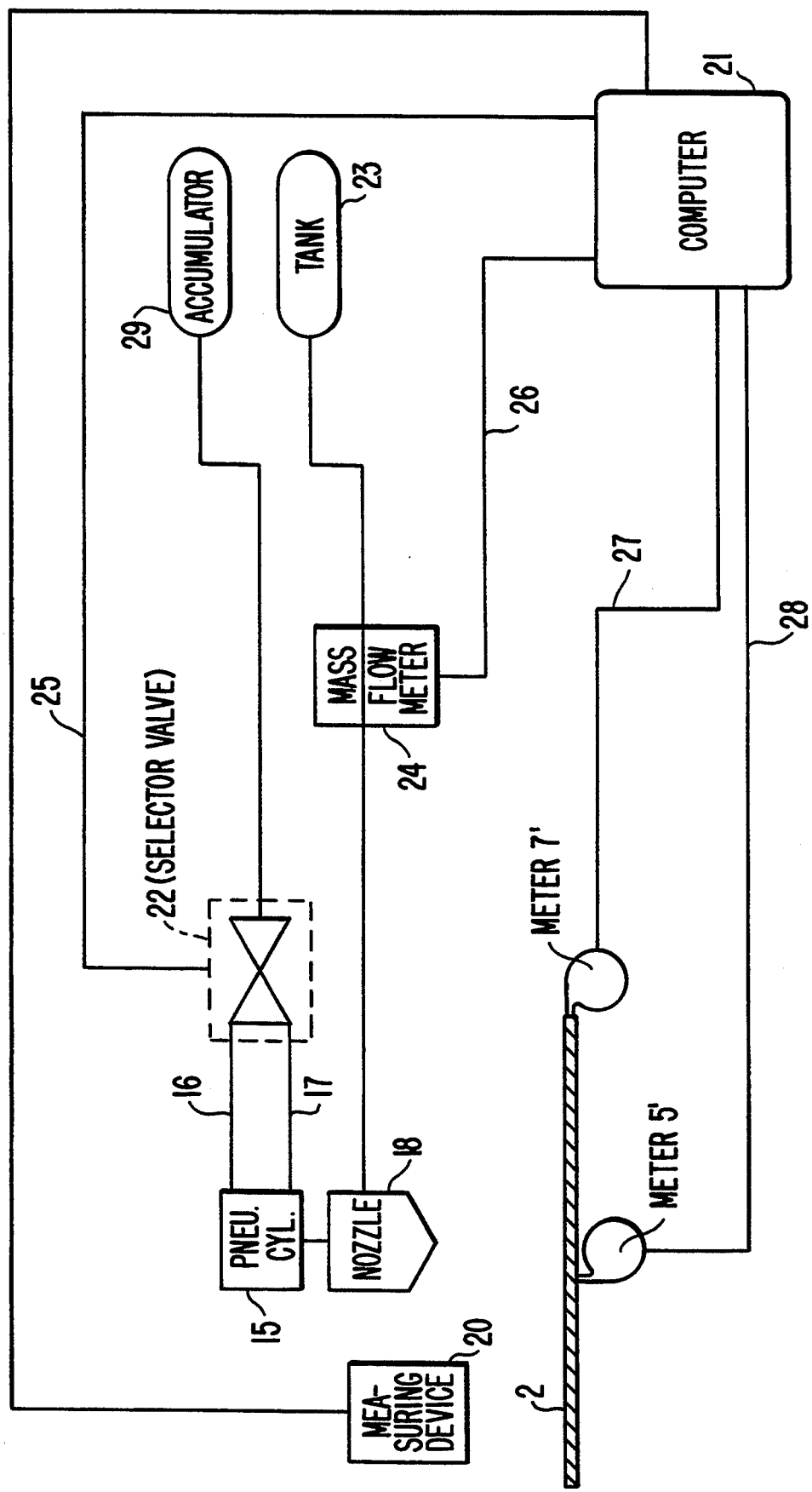
FIG. 3 shows a schematic drawing of the apparatus.

The invention will be further described in the following with reference to FIG. 3 and a more detailed account of the procedure for taking permeability measurements.

Before starting permeability measurements the nozzles to be used must be calibrated against samples with known permeability.

As mentioned initially, permeability measurements are taken automatically and the actual measurement is controlled by means of a computer. When the computer program has been started and the rock sample has been secured, relevant data on the sample are recorded in the computer's memory, i.e. field, well and depth are recorded.

If it is the first time a measurement is taken of a sample, a scanning of the sample should be taken first using the measuring device 20 to determine the positions of the sample's circumference and any holes in the sample. These data are stored in the computer's memory.

In the continuation, physical data on the measurements are defined for the computer. Typical definitions will be the distance between the measuring points in both the X and Y directions and physical measurements and calculation constants for the nozzle or nozzles to be used. The number of times the measurements in each point shall be repeated is to be stated in a preferred performance.

Thereafter the pressure and flow values must be defined for the fluid flow via line 19 and through nozzle 18. In a preferred embodiment, a mass flow meter is used with built-in control valves that can both control and measure pressure and fluid flow through the nozzle. For practical measurements one will chose to maintain either constant pressure or flow rate during the measurement. If constant pressure is chosen one shall chose the gas pressure to be set in each measuring point, and the lower and upper gas flow rate in each measuring point. At a constant flow rate one will similarly specify a value for the gas flow to be set in each measuring point, and the lower and upper limit for gas pressure in each measuring point.

When these data have been entered, measuring may be started.

The sample to be measured is secured to the measuring table 2, 42 and the nozzle's position relative the measuring table is set to zero by moving the nozzle and the measuring table to a centered position in relation to each other. Control of the driving motors or the carriages 44 takes place from the computer, e.g. via cables 27, 28. Then the desired measuring area may be defined. This can be done by defining the position of a rectangle in relation to defined zero setting or simply by moving the measuring table/nozzle to two points that define two corners on the same diagonal in a rectangle.

Measuring can now be started in one corner of the rectangle. The nozzle is moved towards the sample to be measured by air from accumulator 29 that applies pressure on the top of the pneumatic cylinder 15 via selector valve 22 and line 16. The selector valve 22 is controlled by signals from computer 21 via line 25.

When the nozzle 18' is pressed against the rock sample, gas can be admitted from tank 23 (preferably nitrogen gas). The gas flow is controlled, as mentioned previously, via mass flow meter 24 which is controlled from the computer via line 26, and which at the same time is used to send values for pressure and mass flow rates back to the computer.

The measuring results recorded from the gas flow can be used to determine the permeability of the rock sample in a well known manner.

We claim:

1. An apparatus for measuring permeability in rock samples comprising, a measuring table for strapping down a rock sample, a nozzle that can be pressed against the rock sample at a set force, a gas source connected to the nozzle, devices for measuring mass flow through the nozzle and pressure in the nozzle, the apparatus comprising: a rack equipped with a pneumatic cylinder to which the nozzle is attached, the rack and the measuring table being movable in relation to each other along X and Y axes via motors and a computer that controls:
   a) the motors, and thereby the movements of the nozzle and the measuring table relative to each other so that the rock sample is covered by a predetermined measuring point pattern,
   b) a mass flow meter that controls and measures the gas flow to the nozzle, and
   c) a selector valve for compressed air that controls the pneumatic cylinder, and thereby a vertical movement of the nozzle.

2. An apparatus according to claim 1, wherein the rack is mounted to be slidable on a horizontal beam and is moveable between two positions using a pneumatically driven piston-cylinder arrangement.

3. An apparatus according to claim 1, wherein the measuring table comprises a level, fixed table top and side edges, the side edges have mountings for receiving moveable first carriages which are connected to the rack, upon movement of the moveable first carriages the rack moves in a direction of the Y axis, and the rack comprises a horizontal beam on which is mounted a second carriage which is movable along a direction of the X axis.

4. An apparatus according to claim 3, further comprising a first motor located in at least one of the moveable first carriages and a second motor located in the movable second carriage and wherein the first and second motors are controlled on the basis of logical signs from the computer.

5. An apparatus as recited in claim 1, further comprising a support structure upon which the measuring table is located, and wherein the measuring table includes a bottom frame having a driving motor, an intermediate frame having a driving motor and being moveable along the Y axis relative to the bottom frame, and an upper frame being moveable along the X axis relative to the intermediate frame.

6. An apparatus according to claim 5 wherein the driving motor of the bottom frame drives a positioning screw which is oriented in the Y direction and which runs through at least one threaded bushing on the intermediate frame, and the intermediate frame is mounted to be slidable relative to the bottom frame via grooves or guide bars that allow the intermediate frame to slide in the Y direction upon rotation of the positioning screw.

7. An apparatus according to claim 5 wherein the driving motor of the intermediate frame comprises a positioning screw which is oriented along the X axis and which is mounted to be rotatable in a bushing, the positioning screw runs through at least one threaded bushing which is connected to the upper frame, and the upper frame is mounted to be slidable relative to the intermediate frame via grooves or guide bars that allow the upper frame to slide in the X direction upon rotation of the positioning screw.

* * * * *